Figure 1:
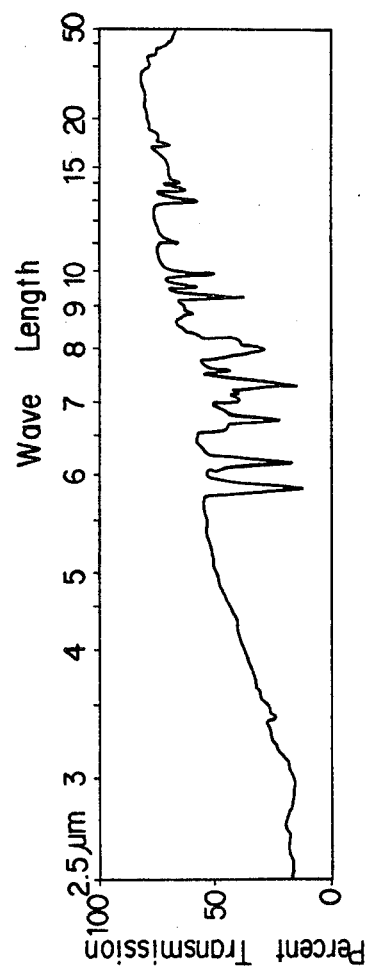

United States Patent [19]

Aoki et al.

[11] Patent Number: 4,481,027

[45] Date of Patent: Nov. 6, 1984

[54] DERIVATIVES OF TETRAHYDROBENZOTHIAZOLE AND HERBICIDAL COMPOSITIONS CONTAINING THE SAME AS AN ACTIVE INGREDIENT

[75] Inventors: Katsumichi Aoki; Yoichi Kanda; Takafumi Shida; Keigo Satake; Hiroyasu Shinkawa, all of Iwaki, Japan

[73] Assignee: Kureha Kagaku Kogyo Kabushiki Kaisha, Tokyo, Japan

[21] Appl. No.: 451,796

[22] Filed: Dec. 21, 1982

[30] Foreign Application Priority Data

Dec. 24, 1981 [JP] Japan ................................ 56-215628
May 10, 1982 [JP] Japan ................................ 57-77798

[51] Int. Cl.³ .................... C07D 417/04; A01N 43/78
[52] U.S. Cl. ........................................ 71/90; 546/270; 548/162
[58] Field of Search ............................ 548/162; 71/90; 546/270

[56] References Cited

U.S. PATENT DOCUMENTS

| | | | |
|---|---|---|---|
| 3,758,492 | 9/1973 | Metzger | 71/90 |
| 3,759,939 | 9/1973 | Metzger | 71/90 |
| 3,990,882 | 11/1976 | Krenzer | 71/90 |
| 4,018,787 | 4/1977 | Krenzer | 71/90 |
| 4,021,439 | 3/1977 | Krenzer | 71/90 |
| 4,029,491 | 6/1977 | Stach | 71/90 |
| 4,045,446 | 8/1977 | Stach | 71/90 |
| 4,167,407 | 9/1979 | Krenzer | 71/90 |
| 4,319,914 | 3/1982 | Stach | 71/90 |

FOREIGN PATENT DOCUMENTS

| | | | |
|---|---|---|---|
| 835155 | 2/1976 | Belgium | 71/90 |
| 175752 | 12/1978 | Czechoslovakia | 71/90 |
| 32879 | 7/1981 | European Pat. Off. | 71/90 |
| 2045754 | 11/1980 | United Kingdom | 71/90 |

*Primary Examiner*—Robert Gerstl
*Attorney, Agent, or Firm*—Cushman, Darby & Cushman

[57] ABSTRACT

Disclosed is a derivative of tetrahydrobenzothiazole represented by the general formula (I):

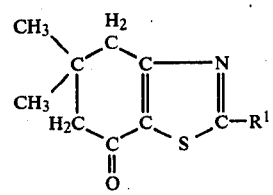

wherein $R^1$ represents one of the following groups:

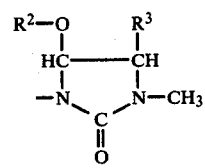

wherein $R^2$ represents a hydrogen atom, methyl group, acetyl group, benzoyl group, phenoxycarbonyl group or 3-pyridylcarbonyl group and $R^3$ represents a hydrogen atom, hydroxy group, methoxy group or acetoxy group,

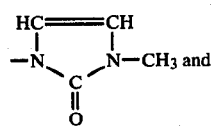

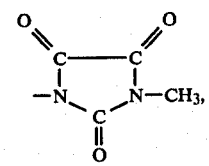

and a herbicidal composition comprising as active ingredient at least one of the derivatives of tetrahydrobenzothiazole.

16 Claims, 12 Drawing Figures

DERIVATIVES OF TETRAHYDROBENZOTHIAZOLE AND HERBICIDAL COMPOSITIONS CONTAINING THE SAME AS AN ACTIVE INGREDIENT

DETAILED EXPLANATION OF THE INVENTION

The present invention relates to a novel derivative of tetrahydrobenzothiazole represented by the general formula (I):

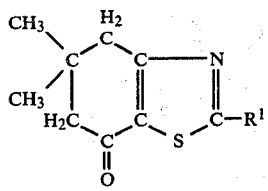

(I)

wherein R¹ represents one of the following groups:

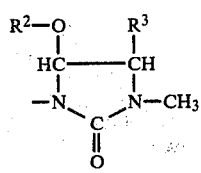

(II)

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

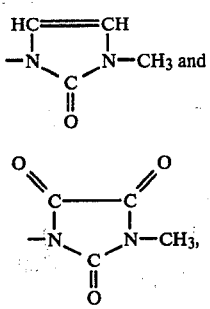

and a herbicidal composition comprising as the active ingredient at least one of the derivatives of tetrahydrobenzothiazole.

As a result of studies on herbicidal composition, the present inventors have found that the derivative of tetrahydrobenzothiazole represented by the general formula (I) has an excellent practical herbicidal effect, and have attained the present invention based on the findings.

The compounds represented by the general formula (I) are novel compounds, and of course, the physiological properties of the compounds have never been known. According to the herbicidal tests consisting essentially of foliar application and soil treatment, the derivatives of tetrahydrobenzothiazole according to the present invention (hereinafter referred to as "the present derivatives") shows an excellent herbicidal activity on broad-leaved weeds, for instance, *Stellaria media, Cardamine flexuosa* and *Portulaca oleracea,* Cyperaceous weeds, for instance, *Cyperus Iria* and Gramineous weeds, for instance, those belonging to the genus Echinochloa and *Poa annua,* and particularly shows strong herbicidal activity when applied on leaves and stems of these weeds. The application is carried out arable lands such as paddy fields, upland fields, orchards, etc. and non-arable lands.

In a first aspect of the present invention, there is provided a derivative of tetrahydrobenzothiazole represented by the general formula (I):

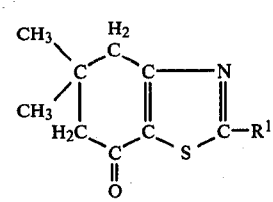

(I)

wherein R¹ represents one of the following groups:

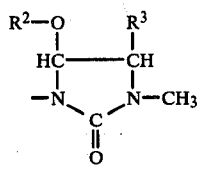

(II)

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

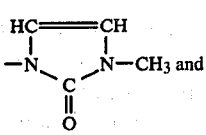

In a second aspect of the present invention, there is provided a herbicidal composition comprising as the active ingredient at least one derivative of tetrahydrobenzothiazole represented by the general formula (I):

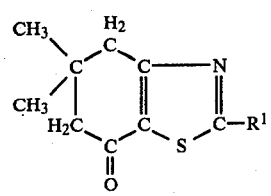

(I)

wherein R¹ represents one of the following groups:

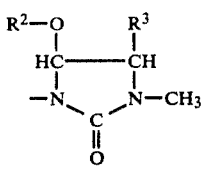

(II)

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

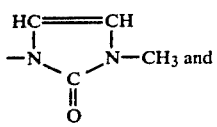

(III)

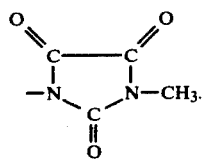

(IV)

The present derivatives having a herbicidal activity, represented by the general formula (I) are synthesized as follows.

Bromodimedone(2-bromo-5,5-dimethyl-1,3-cyclohexanedione) (V) is reacted with a derivative of thiourea,

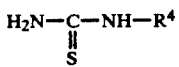

(wherein R⁴ represents a hydrogen atom, methyl group or ethyl group), in ethanol under refluxing condition, or in acetic acid in the presence of sodium acetate at 80° to 90° C. to obtain the following intermediate compound (VI).

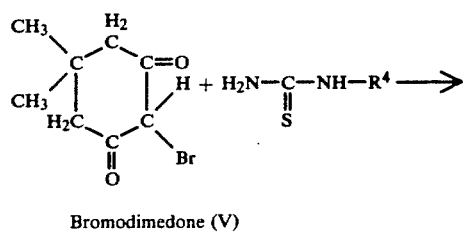

Bromodimedone (V)

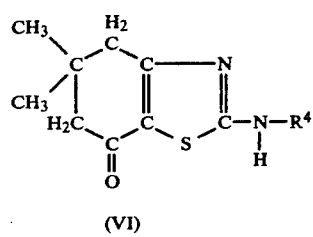

(VI)

The thus obtained intermediate compound (VI) is further reacted with phenyl chloroformate,

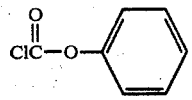

to obtain an intermediate compound (VII).

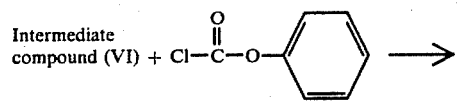

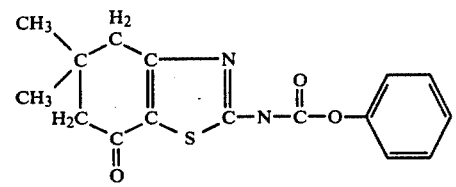

(VII)

In dimethylformamide solvent, phenyl 4,5,6,7-tetrahydro-5,5-dimethyl-7-oxo-2-benzothiazolylcarbamate (VII) which had been synthesized from bromodimedone and thiourea is reacted with methylaminoacetaldehyde dimethylacetal to obtain the intermediate compound (VIII) as follows.

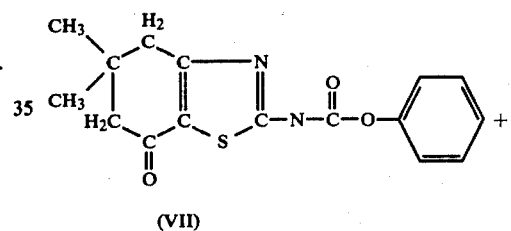

(VII)

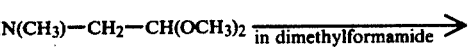

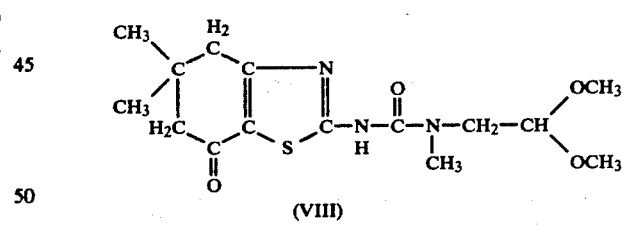

(VIII)

Then, the thus obtained intermediate compound (VIII) is reacted with an alcohol, preferably ethanol in the presence of dilute inorganic acid as follows.

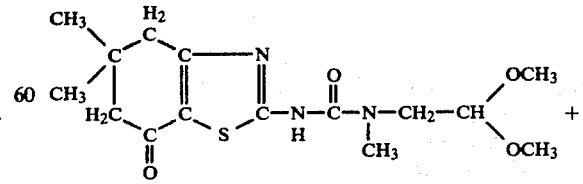

(VIII)

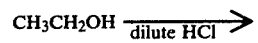

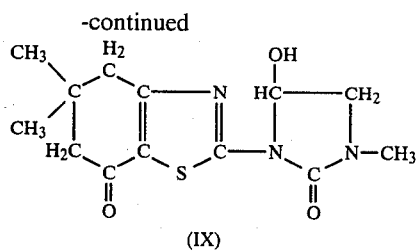

(IX)

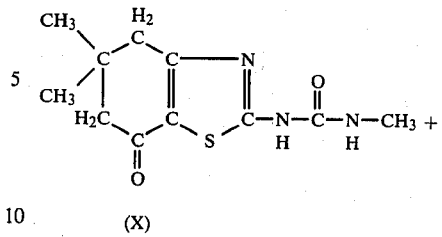

(X)

On the other hand, the compound (VI) wherein $R^4$ represents a hydrogen atom (2-amino-4,5,6,7-tetrahydro-5,5-dimethyl-7-oxo-benzothiazole) is reacted with methylisocyanate in dimethylformamide solvent to obtain the intermediate compound (X) as follows.

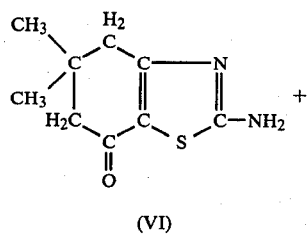

(VI)

$$CH_3NCO \xrightarrow{\text{in dimethylformamide}}$$

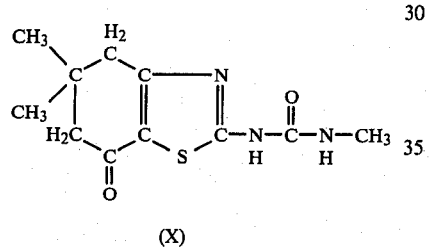

(X)

Then, the thus obtained intermediate compound (X) is reacted with glyoxal, OHC—CHO, as follows.

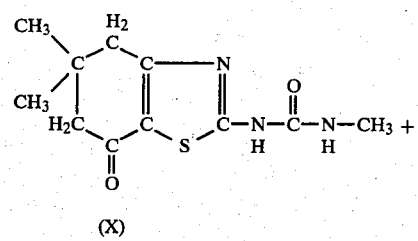

(X)

$$OHC-CHO \longrightarrow$$

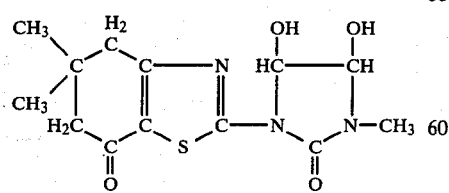

(XI)

Also, the thus obtained intermediate compound (X) is reacted with oxalyl halide, X—CO—CO—X, as follows.

$$X-CO-CO-X \longrightarrow$$

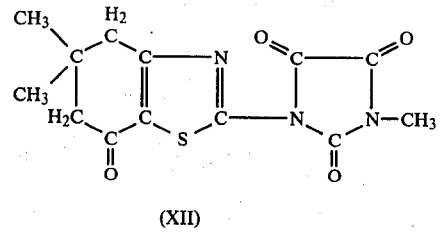

(XII)

Furthermore, the compound (IX) is reacted with an organic acid chloride,

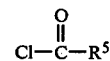

(wherein $R^5$ represents methyl group, phenyl group or phenoxy group) in acetonitrile in the presence of acid-receptor such as tertiary amine, or in basic solvent such as pyridine as follows.

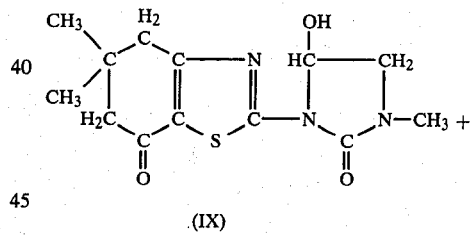

(IX)

$$Cl-\overset{O}{\underset{}{C}}-R^5 \xrightarrow{\substack{\text{in acetonitrile in the} \\ \text{presence of tertiary} \\ \text{amine, or in pyridine}}}$$

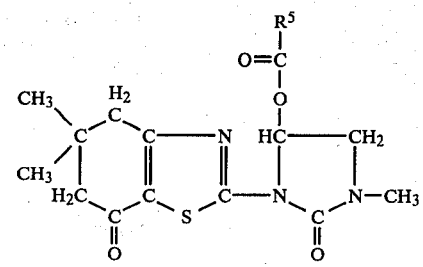

(XIII)

Also, the compound (IX) is reacted with methanol in the presence of catalytic amount of concentrated sulfuric acid as follows.

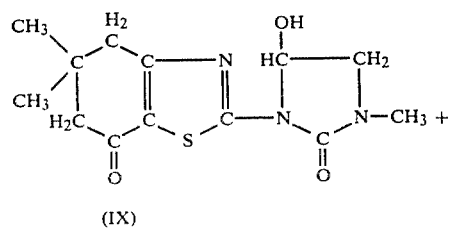

(IX)

CH₃OH $\xrightarrow{\text{conc. sulfuric acid}}$

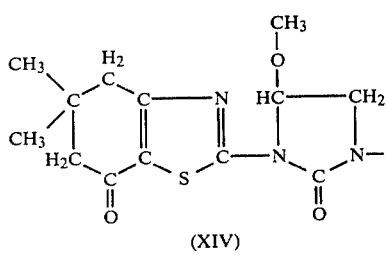

(XIV)

Further, the compound (IX) is reacted with alkyl chloride in basic solvent such as pyridine as follows.

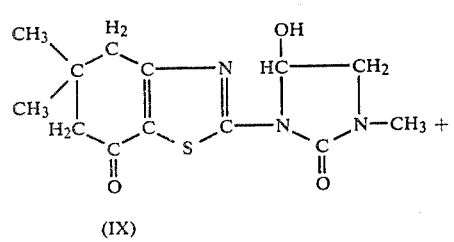

(IX)

R²Cl $\xrightarrow{\text{in pyridine}}$

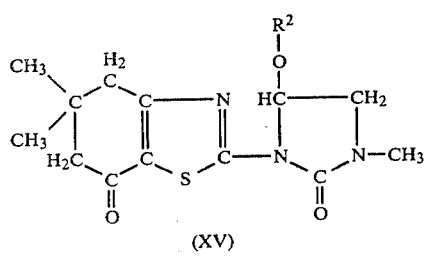

(XV)

The compound (XI) is reacted with methanol in the presence of catalytic amount of concentrated sulfuric acid as follows.

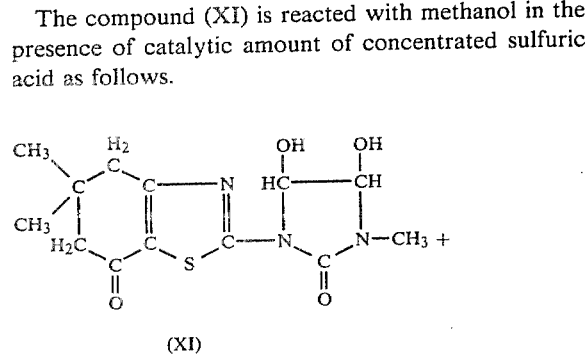

(XI)

CH₃OH $\xrightarrow{\text{conc. sulfuric acid}}$

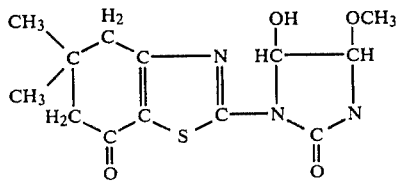

(XVI)

Also, the compound (XI) is reacted with acetyl chloride in basic solvent such as pyridine as follows.

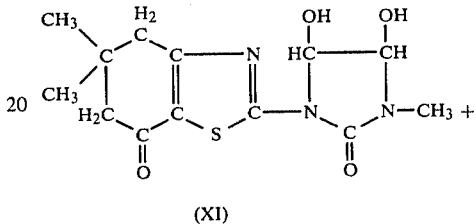

(XI)

CH₃COCl $\xrightarrow{\text{in pyridine}}$

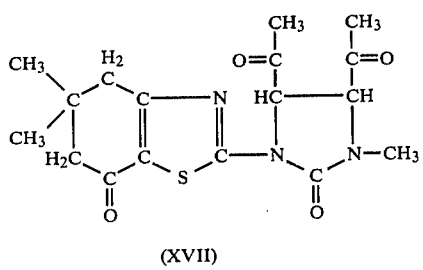

(XVII)

The compound (XVI) is reacted with acetyl chloride in basic solvent such as pyridine as follows.

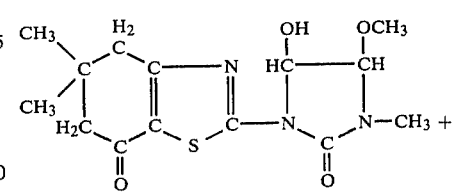

CH₃COCl $\xrightarrow{\text{in pyridine}}$

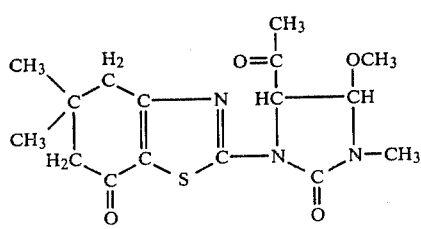

(XVIII)

The present derivatives represented by the general formula (I):

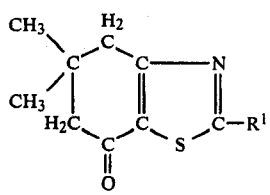

wherein R¹ represents one of the following groups:

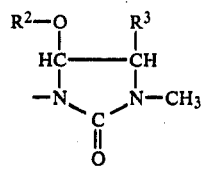

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

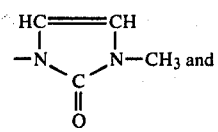

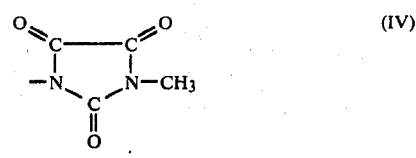

are concretely shown in Table 1 together with their respective melting points.

Infrared absorption spectra of the present derivatives Nos. 1 to 12 are shown respectively in FIGS. 1 to 12.

TABLE 1

Figure 2:
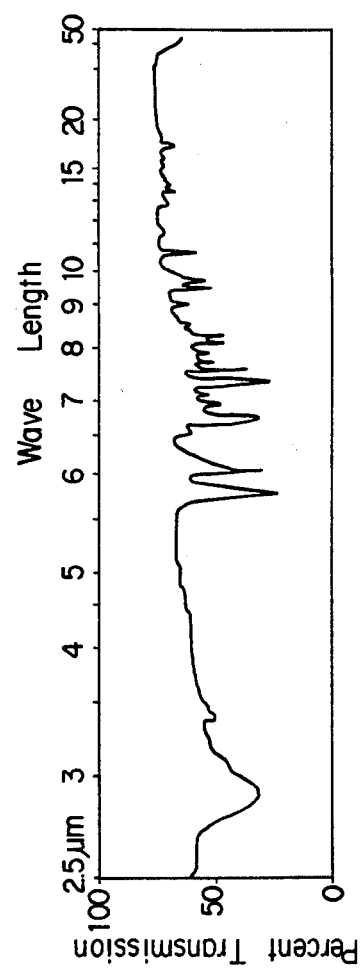
Figure 3:
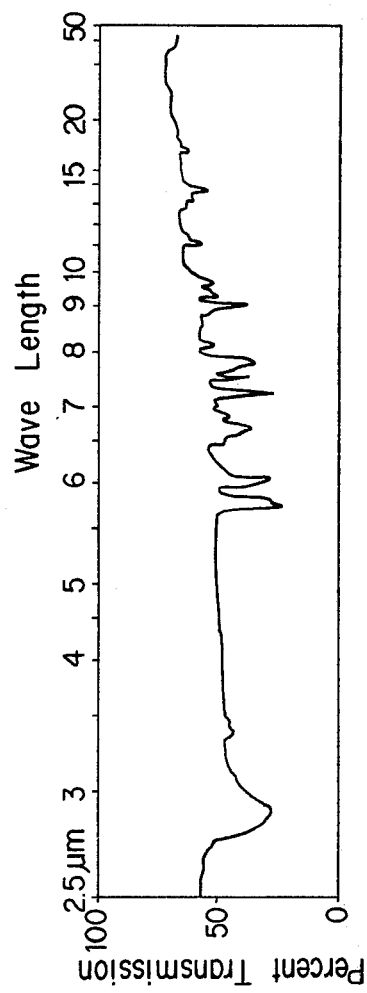
Figure 4:
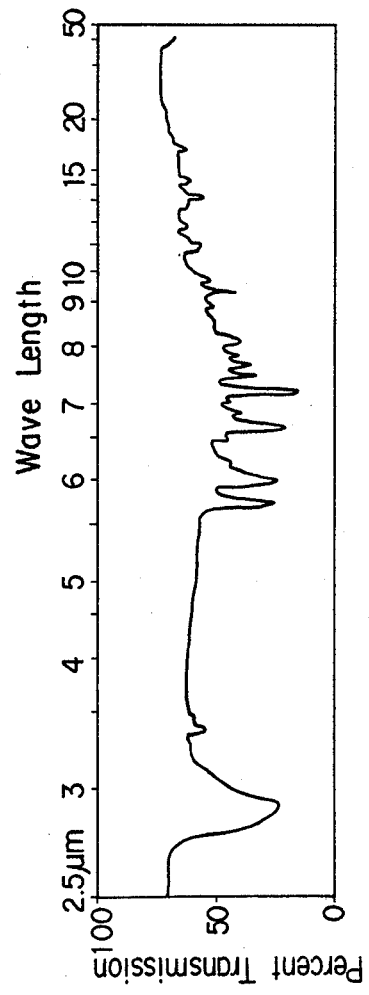
Figure 5:
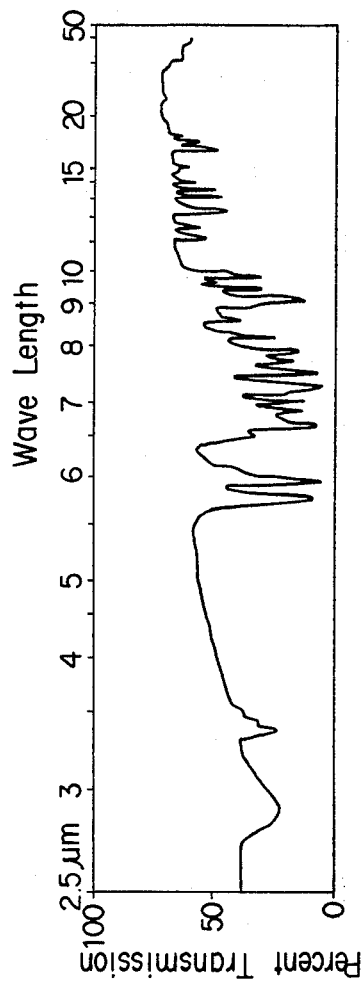

| Number of present derivative | Substituent R¹ | Melting point (°C.) | Elementary analysis C:H:N:S + O | IR |
|---|---|---|---|---|
| 1 |  O—H on HC—CH₂, —N N—CH₃, C=O | 229–230 (with decomposition) | Calculated 52.9:5.8:14.2:27.1 Found 52.9:5.8:14.2:27.1 | FIG. 1 |
| 2 | O—C(=O)—CH₃ on HC—CH₂, —N N—CH₃, C=O | 153–156 | Calculated 54.4:6.1:13.6:25.9 Found 53.4:5.6:12.6:28.4 | FIG. 2 |
| 3 | O—C(=O)—C₆H₅ on HC—CH₂, —N N—CH₃, C=O | 176–178 | Calculated 60.2:5.3:10.5:24.0 Found 60.2:5.3;10.5:24.0 | FIG. 3 |
| 4 | O—C(=O)—O—C₆H₅ on HC—CH₂, —N N—CH₃, C=O | 155–158 | Calculated 57.8:5.1:10.1:27.0 Found 57.8:5.0:10.0:27.2 | FIG. 4 |
| 5 | O—CH₃ on HC—CH₂, —N N—CH₃, C=O | 128–130 (with decomposition) | Calculated 54.4:6.1:13.6:25.9 Found 54.4:6.1:13.6:25.9 | FIG. 5 |

TABLE 1-continued

Figure 6:
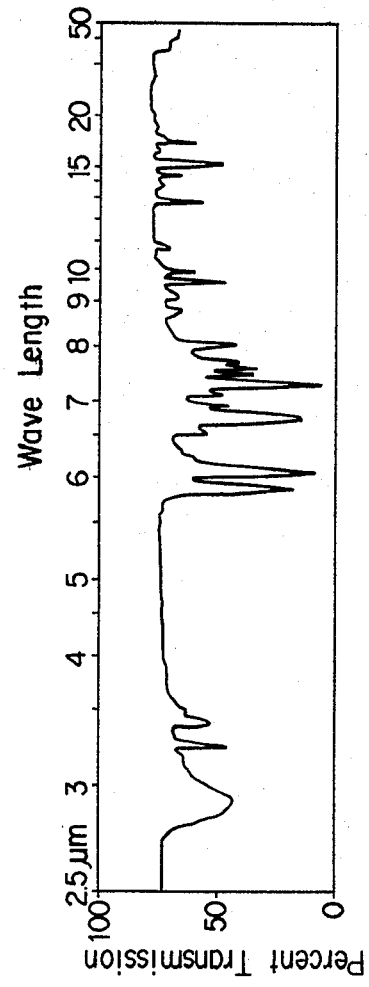
Figure 7:
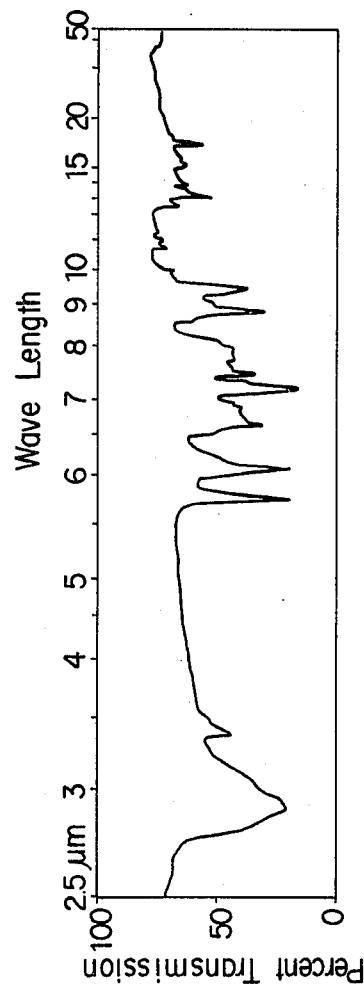
Figure 8:
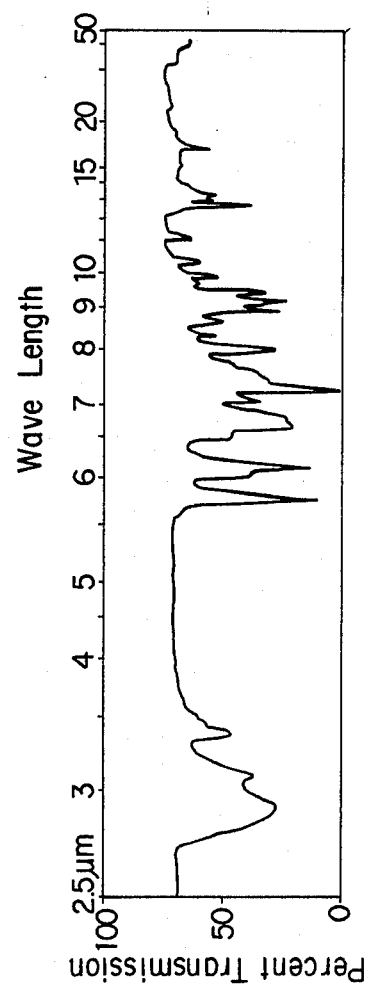
Figures 9, 10:
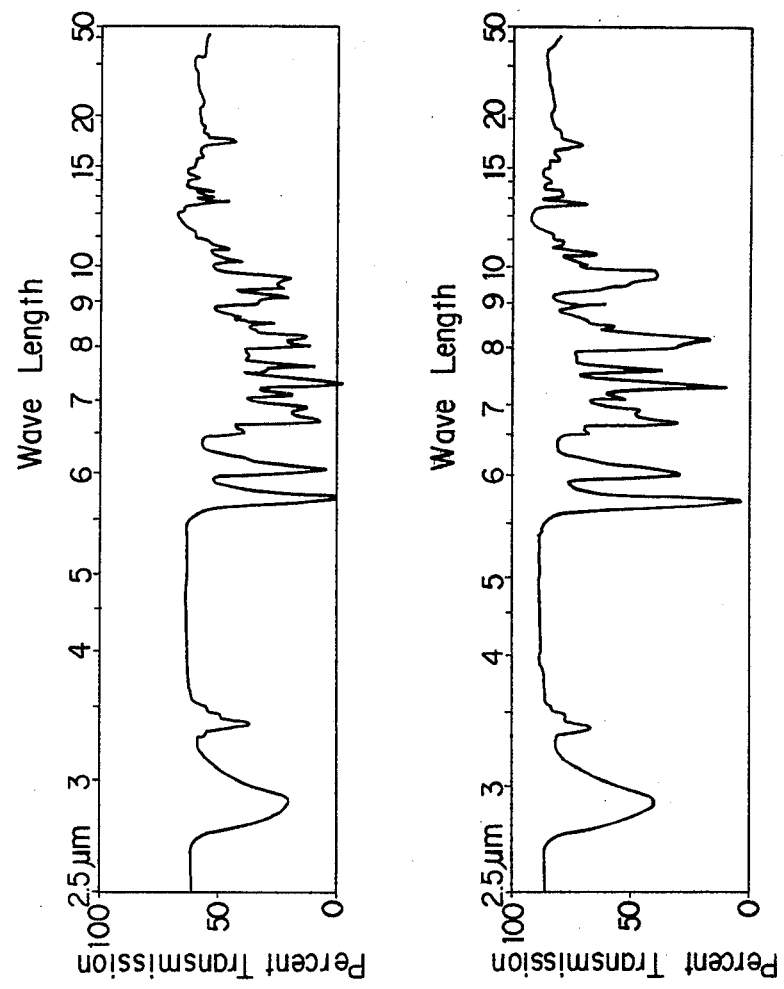
Figure 11:
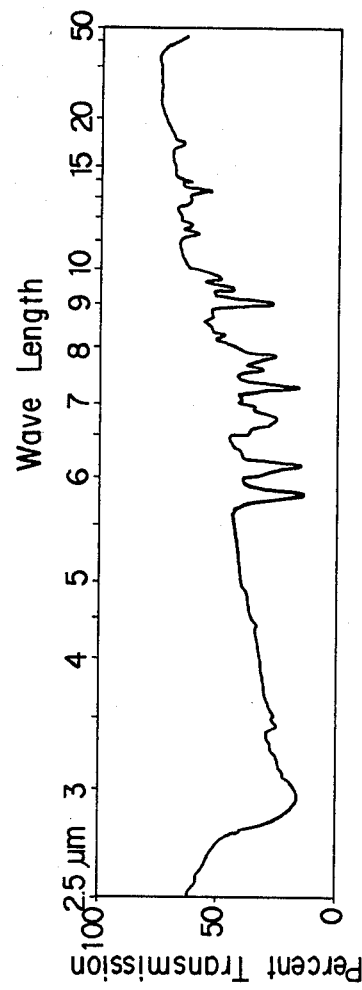
Figure 12:
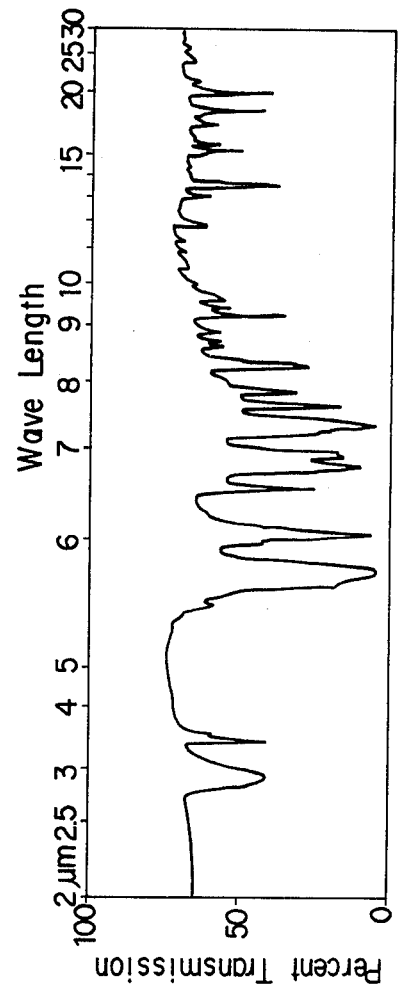

| Number of present derivative | Substituent R¹ | Melting point (°C.) | Elementary analysis C:H:N:S + O | IR |
|---|---|---|---|---|
| 6 | HC=CH, —N(C=O)N—CH₃ | 165–166 | Calculated 56.3:5.4:15.2:23.1 Found 56.3:5.4:15.2:23.1 | FIG. 6 |
| 7 | OH, O—CH₃, HC—CH, —N(C=O)N—CH₃ | 216 (with decomposition) | Calculated 50.2:5.5:13.5:30.8 Found 50.0:5.5:13.5:31.0 | FIG. 7 |
| 8 | OH, O—CH₃, HC—CH, —N(C=O)N—CH₃ | 168–169 | Calculated 51.7:5.8:12.9:29.6 Found 51.7:5.8:13.0:29.5 | FIG. 8 |
| 9 | O—COCH₃, OCH₃, HC—CH, —N(C=O)N—CH₃ | 130–132 | Calculated 52.3:5.7:11.4:30.6 Found 52.3:5.7:11.4:30.6 | FIG. 9 |
| 10 | O—COCH₃, O—COCH₃, HC—CH, —N(C=O)N—CH₃ | 94–96 (with decomposition) | Calculated 51.6:5.3:10.6:32.5 Found 51.6:5.3:10.6:32.5 | FIG. 10 |
| 11 | O—CO-pyridyl, HC—CH₂, —N(C=O)N—CH₃ | 164–165 (with decomposition) | Calculated 57.0:5.0:14.0:24.0 Found 56.9:5.0:14.1:24.0 | FIG. 11 |
| 12 | O=C—C=O, —N(C=O)N—CH₃ | 216–217 | Calculated 50.8:4.2:13.7:31.3 Found 50.8:4.3:13.5:31.4 | FIG. 12 |

Note:
The existence of sulfur was recognized since the present derivatives gave positive result when subjected to the sodium nitroprusside reaction.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

Synthesis of 1-(4,5,6,7-tetrahydro-5,5-dimethyl-7-oxobenzothiazol-2-yl)-3-methyl-5-hydroxy-1,3-imidazolidine-2-one (Present derivative 1)

Into a suspension of 28.8 g (0.09 mol) of phenyl 4,5,6,7-tetrahydro-5,5-dimethyl-7-oxo-benzothiazol-2-yl-carbamate (VII) in 150 ml of dimethylformamide, 16.3 g (0.136 mol) of dimethylacetal of methylaminoacetaldehyde was added, and the mixture was heated for 3 hours under stirring.

After distilling off the solvent, the residue was dissolved in chloroform, and the solution was washed with an aqueous 10% sodium carbonate solution and then with water, and dried on anhydrous sodium sulfate. By distilling off chloroform from the dried solution, 18 g of pale yellow crystals melting at 86°–89° C. were obtained in a yield of 60%. It was confirmed from the infrared absorption spectrum thereof that the crystals were dimethylacetal of 2-[1-methyl-3-(4,5,6,7-tetrahydro-5,5-dimethyl-7-oxo-benzothiazol-2-yl)-ureido]acetaldehyde (VIII).

Absorption maxia of infrared absorption spectrum of the product were as follows (KBr tablet):

$\nu$NH-3380, $\nu$NHCO-1670 and $\nu$CO-1630cm$^{-1}$

Into a mixture of 112.5 ml of ethanol and 150 ml of aqueous 8.8% solution of hydrochloric acid, 18 g (0.053 mol) of the thus obtained compound was dissolved, and after heating the solution under refluxing condition for 30 min, the solution was left as it is in natural cooling to obtain crystals separated out. The crystals were collected by filtration and washed with water and then with warm acetone to be white crystals weighting 6 g and melting at 229° to 230° C. with decomposition. From the infrared absorption spectrum (hereinafter referred to as IR spectrum) and the nuclear magnetic resonance spectrum (hereinafter referred to as NMR spectrum), it was confirmed that the thus obtained compound was present derivative 1.

NMR spectrum (in CDCl$_3$: $\delta$ppm): 1.15 (6H, s: methyl at position 5), 2.47 (2H, s: hydrogen at position 4), 2.79 (2H, s: hydrogen at position 6), 3.01 (3H, s: N-methyl at position 3'), 3.32 to 4.05 (2H, m: hydrogen at position 4'), 4.9 (1H, d, J=2 Hz: hydroxyl at position 5') and 6.11 (1H, dd, J=2 Hz, 7 Hz: hydrogen at position 5'), wherein s means singlet, d means doublet and m means multiplet.

In Examples 1–3, designation of protons appearing in nuclear magnetic resonance spectrum of each derivative was carried out as in the structural formula undermentioned.

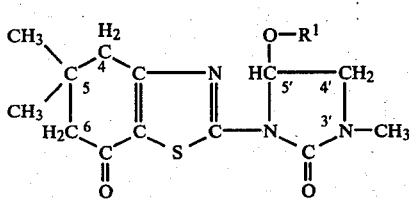

EXAMPLE 2

Synthesis of
1-(4,5,6,7-tetrahydro-5,5-dimethyl-7-oxobenzothiazol-2-yl)-3-methyl-5-benzoyloxy-1,3-imidazolidine-2-one
(Present derivative 3)

Into a solution of 3 g (0.01 mole) of present derivative No. 1 obtained in Example 1 (represented by the formula (IX)) in 60 ml of pyridine, under ice-cooling, 1.7 g (0.012 mol) of benzoyl chloride was added drop by drop, and the mixture was stirred for 10 min. After removing the cooling medium and stirring the mixture for 2 hours, the reaction mixture was poured into 100 ml of water. The thus separated crystals were collected by filtration, washed with water and recrystallized from a mixture of benzene and hexane to be white crystals melting at 176° to 178° C. and weighing 1.8 g.

It was confirmed from IR spectrum and NMR spectrum thereof that the crystals were present derivative 3.

NMR spectrum (in CDCl$_3$: $\delta$ppm): 1.1 (6H, s: methyl at position 5), 2.47 (2H, s: hydrogen at position 4), 2.75 (2H, s: hydrogen at position 6), 3.11 (3H, s: N-methyl at position 3'), 3.71 (1H, dd, J=2 Hz: hydrogen at position 4'), 4.12 (1H, dd, J=7 Hz, 11 Hz: hydrogen at position 4'), 7.41 (1H, dd, J=2 Hz, 7 Hz: hydrogen at position 5') and 7.49 to 8.31 (5H, m: aromatic protons)

EXAMPLE 3

Synthesis of
1-(4,5,6,7-tetrahydro-5,5-dimethyl-7-oxobenzothiazol-2-yl)-3-methyl-5-methoxy-1,3-imidazolidine-2-one
(Present derivative 5)

After having a solution of 3 g (0.01 mol) of present derivative No. 1 (represented by the general formula (IX)) in 120 ml of anhydrous methanol under refluxing condition in the presence of a catalytic amount of concentrated sulfuric acid, the reaction mixture was left as it is to separate out crystals which were collected by filtration. The thus obtained white crystals showed a melting point of 128° to 130° C. with decomposition. The yield was 2.1 g.

It was confirmed from the IR spectrum and the NMR spectrum thereof that the thus obtained crytals were present derivative 5.

NMR spectrum (in CDCl$_3$: $\delta$ppm): 1.13 and 1.16 (6H, s: methyl at position 5), 2.47 (2H, s: hydrogen at position 4), 2.83 (2H, s: hydrogen at position 6), 3.0 (3H, s: N-methyl at position 3'), 3.5 (1H, dd, J=2 Hz, 11 Hz: hydrogen at position 4'), 3.59 (3H, s: O-methyl at position 5'), 3.8 (1H, dd, J=7 Hz, 11 Hz: hydrogen at position 4') and 5.99 (1H, dd, J=2 Hz, 7 Hz: hydrogen at position 5').

EXAMPLE 4

Synthesis of
1-(4,5,6,7-tetrahydro-5,5-dimethyl-7-oxo-2-benzothiazol-2-yl)-3-methyl-4,5-dihydroxy-1,3-imidazolidine-2-one (present derivative 7)

Into 150 ml of ethanol, 5 g (0.02 mol) of N-methyl-N'-(4,5,6,7-tetrahydro-5,5-dimethyl-7-oxo-2-benzothiazolyl)urea (represented by the formula (X)) was added under stirring to prepare a suspension, and an aqueous 40% solution of glyoxal adjusted to pH of 8 to 9 was added drop by drop to the suspension. After heating the mixture under refluxing condition for 7 hours, ethanol was distilled off from the reaction mixture and the residue was extracted with chloroform. By treating the chloroform-extract with a series of conventional procedures, white crystals melting at 216° C. with decomposition were obtained in an amount of 4.1 g, which was identified by IR spectrum and NMR spectrum thereof as present derivative 7.

NMR spectrum (DMSO-d$_6$): $\delta$ppm are as follows: 1.06 (s, 6H: CH$_3$ at Position 5), 2.44 (s, 2H: H at Position 4), 2.83 (s, 2H: H at Position 6), 2.92 (s, 3H: N—CH$_3$ at Position 3'), 4.86 (m, 1H: H at Position 4'), 5.6 (m, 1H: H at Position 5'), 6.77 (m, 1H: O—H at position 4') and 7.37 (m, 1H: O—H at Position 5').

EXAMPLE 5

Synthesis of 1-(4,5,6,7-tetrahydro-5,5-dimethyl-7-oxo-2-benzothiazol-2-yl)-3-methyl-1,3-imidazolidine-2,4,5-trione (present derivative 12)

Into 30 ml of chloroform, 2.1 g (0.0084 mol) of N-methyl-N'-(4,5,6,7-tetrahydro-5,5-dimethyl-7-oxo-2-benzothiazolyl)urea (represented by the formula (X)) and 1.2 g (0.009 mol) of oxalyl chloride were added, and the mixture was heated under refluxing condition for 30 min.

After leaving the reaction mixture to cool, n-hexane was added to the reaction mixture to educe the crystals, which were collected by filteration and recrystallized from a mixed solvent consisting of dimthylformamide and ethanol to obtain 2.4 g of white crystals melting at 216° to 217° C.

The thus obtained product was identified as present derivative 12 from the IR spectrum and the NMR spectrum thereof.

NMR spectrum (DMSO-$d_6$): δppm are as follows: 1.1 (s, 6H: $CH_3$ at Position 5), 2.51 (s, 2H: H at Position 4), 2.93 (s, 2H: H at Position 6) and 3.11 (s, 3H: N—$CH_3$ at Position 38).

In the cases where the present derivative represented by the general formula (I) is used as a herbicide, the derivative itself or a composition thereof suitably diluted by a diluent may be applied by a means such as scattering, and also according to the necessity, a composition prepared by further admixing additives such as spreader, wetting agent, sticking agent, etc. may be applied.

In addition, there is no possibility of decomposition or denaturation of the present derivative by the other agricultural chemical(s) admixed there with, or decomposition or denaturation of the other agricultural chemicals by the present derivative admixed therewith, and accordingly, any other physiologically active agents, for instance, fungicide(s), insecticide(s), bactericide(s), herbicide(s), plant growth regulator(s), etc. or fertilizer(s) can be admixed therewith or can be used in combination in application.

The present invention will be further explained while referring to the preparation examples of the herbicidal compositions wherein the kinds of the active ingredients and additives and the mixing ratio in the composition can be selected from the broad range.

PREPARATION EXAMPLE 1

Preparation and use of a wettable powder

By mixing 50 parts by weight of present derivative 1, 5 parts by weight of a salt of ligninsulfonic acid, 3 parts by weight of a salt of alkylsulfonic acid and 42 parts by weight of diatomaceous earth and pulferizing the mixture, a wettable powder was prepared.

The thus prepared wettable powder is applied after diluting with water to a suitable concentration of present derivative 1 as the active ingredient.

PREPARATION EXAMPLE 2

Preparation and application of an emulsifiable concentrate

By uniformly mixing 25 parts by weight of present derivative 2, 65 parts by weight of xylene and 10 parts by weight of polyoxyethylenealkyl aryl ether, an emulsifiable concentrate was prepared.

The thus prepared emulsifiable concentrate is applied after diluting with water to a suitable concentration of the active ingredient.

PREPARATION EXAMPLE 3

Preparation and application of a granular composition

After uniformly mixing 8 parts by weight of present derivative 3, 40 parts by weight of bentonite, 45 parts by weight of clay and 7 parts by weight of a salt of ligninsulfonic acid, the mixture was kneaded with water and processed into granules by an extruding granulator. The granules were dried and sifted to be a product of granular composition which is directly applied.

The effectiveness of the present derivative is explained while referring to the herbicidal test examples as follows.

HERBICIDAL TEST EXAMPLE 1

Herbicidal test example by foliar application

To the follage of each of the following plants grown from their seeds under a management in a plastic planter of 180×580×150 mm in size filled with a soil collected from an actual crop field, each of the wettable powders prepared as in Preparation Example 1 and diluted respectively to 0.1 and 0.2% by weight of the active ingredient with water was sprayed by a small pressured-sprayer at a rate of 10 liters per are of the surface of the soil in the plastic planter kept in a glass house.

After 20 days of the treatment, the state of the plants was observed to assess the damage due to the application of each of the wettable powders to find out the herbicidal activity thereof according to the following criteria:

| Criteria of herbicidal activity | |
|---|---|
| Index | Phytotoxicity |
| 0 | none |
| 1 | minute |
| 2 | slight |
| 3 | medium |
| 4 | severe |
| 5 | very severe (withered) |

| Name of the plants tested | |
|---|---|
| 1. Echinochloa crus-galli | 2. Digitaria ciliaris |
| 3. Poa annua | 4. Portulaca oleracea |
| 5. Chenopodium album | 6. Amaranthus lividus |
| 7. Polygonum longisetun | 8. Cardamine flexuosa |
| 9. Triticum aestivum (Wheat) | 10. Zea mays (Maize) |
| 11. Gossypium arboreum (Cotton) | |

The herbicidal activities of the present derivatives thus assessed are shown in Table 2. The growth state of the plants when the present wettable powders were applied was as follows.

| Those in 2 to 3 leaf-stage: | |
|---|---|
| Echinochloa crus-galli | Digitaria ciliaris |
| Poa annua | Portulaca oleracea |
| Chenopodium album | Amaranthus lividus |
| Polygonum longisetum | |
| Triticum aestivum and Zea mays | |
| That in 3 to 4 leaf-stage: | |
| Cardamine flexuosa | |
| That in the first true leaf-stage: | |
| Gossypium arboreum | |

TABLE 2

| | Herbicidal Activity Present derivative | | | | | | | | | | | | Not treated |
|---|---|---|---|---|---|---|---|---|---|---|---|---|---|
| | 1 | | 2 | | 3 | | 4 | | 5 | | 6 | | |
| | Concentration % | | | | | | | | | | | | |
| Plant | 0.1* | 0.2 | 0.1 | 0.2 | 0.1 | 0.2 | 0.1 | 0.2 | 0.1 | 0.2 | 0.1 | 0.2 | — |
| Echinochloa crus-galli | 1 | 3 | 4 | 4 | 1 | 2 | 0 | 2 | 2 | 3 | 1 | 3 | 0 |
| Digitaria ciliaris | 2 | 3 | 3 | 4 | 0 | 2 | 2 | 3 | 3 | 3 | 2 | 3 | 0 |
| Poa annua | 3 | 4 | 4 | 5 | 1 | 3 | 1 | 3 | 3 | 4 | 1 | 3 | 0 |
| Portulaca oleracea | 3 | 4 | 4 | 5 | 0 | 1 | 4 | 5 | 3 | 5 | 2 | 4 | 0 |
| Chenoposium album | 5 | 5 | 5 | 5 | 2 | 3 | 2 | 4 | 5 | 5 | 3 | 4 | 0 |
| Amaranthus lividus | 5 | 5 | 5 | 5 | 2 | 2 | 3 | 4 | 5 | 5 | 3 | 4 | 0 |
| Polygonum longisetum | 5 | 5 | 5 | 5 | 0 | 2 | 3 | 4 | 5 | 5 | 3 | 4 | 0 |
| Cardamine flexuosa | 4 | 5 | 4 | 5 | 2 | 3 | 5 | 5 | 4 | 5 | 4 | 5 | 0 |
| Triticum aestivum | 3 | 4 | 4 | 4 | 0 | 0 | 0 | 0 | 2 | 4 | 3 | 3 | 0 |
| Zea mays | 0 | 0 | 0 | 0 | 0 | 1 | 0 | 0 | 0 | 0 | 0 | 0 | 0 |
| Gossypium arboreum | 5 | 5 | 5 | 5 | 1 | 1 | 4 | 4 | 5 | 5 | 4 | 4 | 0 |

Note:
Concentration, % by weight, of each active ingredient in the dilute wettable power with water, applied to the plants.

HERBICIDAL TEST EXAMPLE 2

Herbicidal tests by foliar application of the present compound

To the seedlings of the plants shown below respectively grown from the seeds sown in a soil collected from a field and packed in a planter of a size of 650×210×200 mm, under a growth management in a green house, an aqueous suspension containing 0.2% by weight of each of the present compound prepared by diluting each of the wettable powders (so-called wettable compositions) prepared as Preparation Example 1 was sprayed from a small sprayer at a rate of 10 liters per are of the soil surface to sufficiently wet the foliage of the plants. After 20 days of the treatment, the state of the plants was surveyed according to the following standard of phytotoxic symptoms.

For reference, the growth state of the respective plant species at the time of spraying was as follows.
Growth state:

| Species | State of growth |
|---|---|
| Echinochloa crus-galli | 2-3 leaf stage |
| Poa annua | 2-3 leaf stage |
| Stellaria media | 5-6 leaf stage |
| Portulaca oleracea | 5-6 leaf stage |
| Cardamine flexuosa | 5-6 leaf stage |
| Rice | 2-3 leaf stage |
| Wheat | 2-3 leaf stage |
| Maize | 2-3 leaf stage |
| Cucumber | 2-3 leaf stage |
| Tomato | 2-3 leaf stage |

Standard of recording phytotoxic symptoms.

| Index | Phytotoxicity |
|---|---|
| 0 | none |
| 1 | minute |
| 2 | slight |
| 3 | medium |
| 4 | severe |
| 5 | very severe (withered) |

The results of survey of phytotoxicity are shown in Table 3.

TABLE 3

| | Herbicidal Activity Present derivative No. | | | | | | Not treated |
|---|---|---|---|---|---|---|---|
| Plant | 7 | 8 | 9 | 10 | 11 | 12 | |
| Echinochloa crus-galli | 5 | 4 | 4 | 3 | 5 | 2 | 0 |
| Poa annua | 5 | 3 | 4 | 3 | 5 | 2 | 0 |
| Stellaria media | 5 | 5 | 5 | 4 | 4 | 5 | 0 |
| Portulaca oleracea | 5 | 5 | 5 | 4 | 3 | 5 | 0 |
| Cardamine flexuosa | 5 | 5 | 5 | 4 | 5 | 5 | 0 |
| Rice | 5 | 4 | 5 | 3 | 4 | 5 | 0 |
| Wheat | 5 | 3 | 3 | 3 | 3 | 5 | 0 |
| Maize | 5 | 2 | 5 | 4 | 0 | 1 | 0 |
| Cucumber | 5 | 5 | 4 | 5 | 2 | 5 | 0 |
| Tomato | 5 | 5 | 5 | 5 | 5 | 5 | 0 |

HERBICIDAL TEST EXAMPLE 3

Herbicidal tests by foliar application of the present compound

To the seedlings of the plants shown below respectively grown from the seeds sown in a field (1 m×1 m), an aqueous suspension containing respective 0.5 and 0.1% by weight of each of the present compound prepared by diluting each of the wettable powders (so-called wettable compositions) prepared as Preparation Example 1 and alkylphenolpolyethylene glycolether as a spreader agent was sprayed from a small sprayer at a rate of 10 liters per are of the soil surface to sufficiently wet the foliage of the plants. After 20 days of the treatment, the plants of the remaining treated plants above ground were weight (without drying) and the value thereof represented by A g/unit area was compared with that of the untreated plants represented by B g/unit area.

The results are shown by A/B (%) in Table 4.

TABLE 4

| | Present derivative No. | | | | | | | | | | | | | | | | |
|---|---|---|---|---|---|---|---|---|---|---|---|---|---|---|---|---|---|
| | 1 | | 2 | | 4 | | 5 | | 7 | | 8 | | 9 | | 10 | | 12 |
| | Concentration (%) | | | | | | | | | | | | | | | | |
| Plant | 0.05 | 0.1 | 0.05 | 0.1 | 0.05 | 0.1 | 0.05 | 0.1 | 0.05 | 0.01 | 0.05 | 0.1 | 0.05 | 0.1 | 0.05 | 0.1 | 0.05 | 0.1 |
| Portulaca oleracea | 0 | 0 | 0 | 0 | 35 | 0 | 33 | 0 | 0 | 0 | 0 | 0 | 0 | 0 | 19 | 0 | 0 | 0 |

TABLE 4-continued

| | Present derivative No. | | | | | | | | | | | | | | | | |
|---|---|---|---|---|---|---|---|---|---|---|---|---|---|---|---|---|---|
| | 1 | | 2 | | 4 | | 5 | | 7 | | 8 | | 9 | | 10 | | 12 |
| | Concentration (%) | | | | | | | | | | | | | | | | |
| Plant | 0.05 | 0.1 | 0.05 | 0.1 | 0.05 | 0.1 | 0.05 | 0.1 | 0.05 | 0.01 | 0.05 | 0.1 | 0.05 | 0.1 | 0.05 | 0.1 | 0.05 | 0.1 |
| *Amaranthus lividus* | 0 | 0 | 0 | 0 | 87 | 55 | 43 | 0 | 0 | 0 | 11 | 0 | 14 | 9 | 23 | 5 | 0 | 0 |
| *Chenopodium album* | 0 | 0 | 0 | 0 | 93 | 86 | 45 | 0 | 0 | 0 | 14 | 0 | 17 | 0 | 13 | 7 | 0 | 0 |
| Glycine max (Soybean) | 98 | 96 | 109 | 97 | 96 | 96 | 111 | 103 | 84 | 39 | 93 | 91 | 97 | 93 | 98 | 91 | 102 | 100 |
| Glycine max (Soybean) | 115 | 97 | 93 | 95 | 97 | 94 | 102 | 99 | 92 | 48 | 99 | 97 | 96 | 94 | 96 | 94 | 109 | 98 |

What is claimed is:

1. A derivative of tetrahydrobenzothiazole represented by the general formula (I):

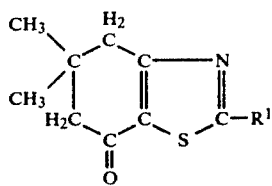

wherein R¹ represents one of the following groups:

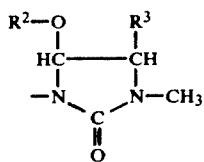

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

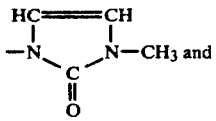

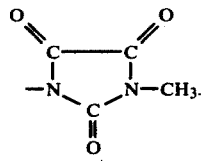

2. 1-(4,5,6,7-tetrahydro-5,5-dimethyl-7-oxo-2-benzothiazol-2-yl)-3-methyl-5-hydroxy-1,3-imidazolidine-2-one.

3. 1-(4,5,6,7-tetrahydro-5,5-dimethyl-7-oxo-2-benzothiazol-2-yl)-3-methyl-5-acetoxy-1,3-imidazolidine-2-one.

4. 1-(4,5,6,7-tetrahydro-5,5-dimethyl-7-oxo-2-benzothiazol-2-yl)-3-methyl-5-benzoyloxy-1,3-imidazolidine-2-one.

5. 1-(4,5,6,7-tetrahydro-5,5-dimethyl-7-oxo-2-benzothiazol-2-yl)-3-methyl-5-phenoxycarbonyloxy-1,3-imidazolidine-2-one.

6. 1-(4,5,6,7-tetrahydro-5,5-dimethyl-7-oxo-2-benzothiazol-2-yl)-3-methyl-5-methoxy-1,3-imidazolidine-2-one.

7. 1-(4,5,6,7-tetrahydro-5,5-dimethyl-7-oxo-2-benzothiazol-2-yl)-3-methyl-4,5-hydroxy-1,3-imidazolidine-2-one.

8. 1-(4,5,6,7-tetrahydro-5,5-dimethyl-7-oxo-2-benzothiazol-2-yl)-3-methyl-4-methoxy-5-hydroxy-1,3-imidazolidine-2-one.

9. 1-(4,5,6,7-tetrahydro-5,5-dimethyl-7-oxo-2-benzothiazol-2-yl)-3-methyl-4-methoxy-5-acetoxy-1,3-imidazolidine-2-one.

10. 1-(4,5,6,7-tetrahydro-5,5-dimethyl-7-oxo-2-benzothiazol-2-yl)-3-methyl-4,5-acetoxy-1,3-imidazolidine-2-one.

11. 1-(4,5,6,7-tetrahydro-5,5-dimethyl-7-oxo-2-benzothiazol-2-yl)-3-methyl-5-(3-pyridylcarbonyl)oxy-1,3-imidazolidine-2-one.

12. 1-(4,5,6,7-tetrahydro-5,5-dimethyl-7-oxo-2-benzothiazol-2-yl)-3-methyl-1,3-imidazolone-2-one.

13. 1-(4,5,6,7-tetrahydro-5,5-dimethyl-7-oxo-2-benzothiazol-2-yl)-3-methyl-1,3-imidazolidine-2,4,5-trione.

14. A herbicidal composition comprising as the active ingredient at least one derivative of tetrahydrobenzothiazole represented by the general formula (I):

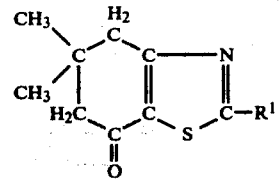

wherein R¹ represents one of the following groups:

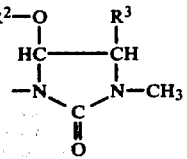

wherein R² represents a hydrogen atom, methyl group, acetyl group, benzoyl group, phenoxycarbonyl group or 3-pyridylcarbonyl group and R³ represents a hydrogen atom, hydroxy group, methoxy group or acetoxy group,

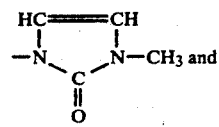

-continued

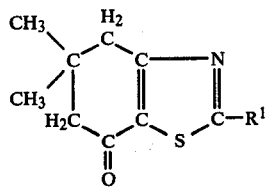 (IV)

together with an herbicidally acceptable carrier or diluent.

15. A method of controlling weeds in an area infested therewith comprising applying to said area an herbicide composition comprising as an active ingredient a tetrahydrobenzothiazole represented by the formula:

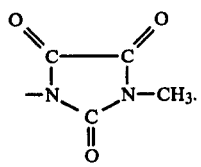 (I)

wherein $R^1$ represents one of the following groups:

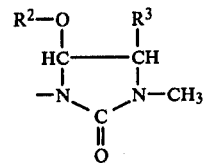 (II)

wherein $R^2$ represents a hydrogen atom, methyl group, acetyl group, benzoyl group, phenoxycarbonyl group or 3-pyridylcarbonyl group and $R^3$ represents a hydrogen atom, hydroxy group, methoxy group or acetoxy group,

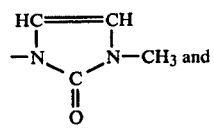 (III)

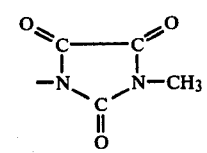 (IV)

together with an herbicidally acceptable carrier or diluent.

16. The method of claim 15 in which broad-leaved weeds are controlled.

* * * * *